United States Patent [19]

Sallmann et al.

[11] Patent Number: 5,369,117
[45] Date of Patent: Nov. 29, 1994

[54] 5-(3-FORMYLAMINO-4-HYDROXY-PHENYL)-3-(1-(4-METHOXYPHENYL)-PROP-2-YL)-OXAZOLIDINES

[75] Inventors: Alfred Sallmann, Bottmingen; Hans-Peter Gschwind, Basel; Eric Francotte, Nuglar, all of Switzerland

[73] Assignee: Ciba-Geigy Corporation, Ardsley, N.Y.

[21] Appl. No.: 107,552

[22] Filed: Aug. 17, 1993

[30] Foreign Application Priority Data

Sep. 2, 1992 [CH] Switzerland .................. 2742/92-9

[51] Int. Cl.$^5$ .................................. C07D 263/06
[52] U.S. Cl. .................................. 514/374; 548/215; 548/216
[58] Field of Search .................. 548/215, 216; 514/374

[56] References Cited

U.S. PATENT DOCUMENTS

| | | |
|---|---|---|
| 3,994,974 | 11/1976 | Murakami et al. |
| 4,219,655 | 8/1980 | Teach ..................... 548/215 |
| 4,407,819 | 10/1983 | Kiernan et al. .......... 548/215 |
| 4,705,798 | 10/1987 | Schoenwald et al. .... 548/215 |
| 5,066,793 | 11/1991 | Francotte et al. ........ 536/50 |
| 5,091,520 | 2/1992 | Francotte et al. ........ 536/56 |

FOREIGN PATENT DOCUMENTS

245784  6/1969  U.S.S.R. .................. 548/215

OTHER PUBLICATIONS

Johansen et al., Prodrugs as Drug Delivery Systems XXV: Hydrolysis of Oxazolidines-A Potential New Prodrug Type, J. Pharmaceutical Sciences 72, pp. 1294-1298 (1983).

Murase et al, New β-Adrenoreceptor Stimulants, Studies on 3-Acylamino-4-Hydroxy-α-(N-Substituted Aminomethyl)Benzyl Alcohols, Chem. Pharm. Bull. 25, pp. 1368-1377 (1977).

*Primary Examiner*—Donald G. Daus
*Attorney, Agent, or Firm*—Irving M. Fishman; Karen G. Kaiser

[57] ABSTRACT

The present invention relates to novel oxazolidines of formula (1)

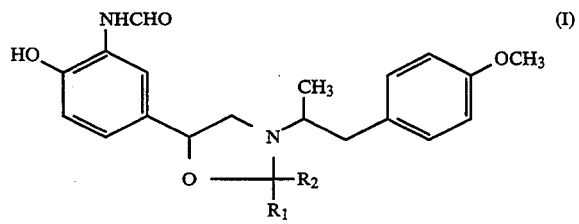

wherein $R_1$ and $R_2$ are simultaneously hydrogen or both are the same lower alkyl radical or together are 4- to 7-membered lower alkylene, and to the salts thereof in racemic and chiral form, to the preparation of these novel compounds, to pharmaceutical compositions containing them and to the use thereof as medicaments. The compounds have a stimulating effect on beta-adrenergic receptors and can be used, inter alia, for the treatment of diseases associated with reversible obstruction of the respiratory tract, typically asthma and chronic bronchitis, and also for inflammations of different origin.

7 Claims, No Drawings

5-(3-FORMYLAMINO-4-HYDROXYPHENYL)-3-(1-(4-METHOXYPHENYL)PROP-2-YL)-OXAZOLIDINES

The present invention relates to novel oxazolidines of formula (I)

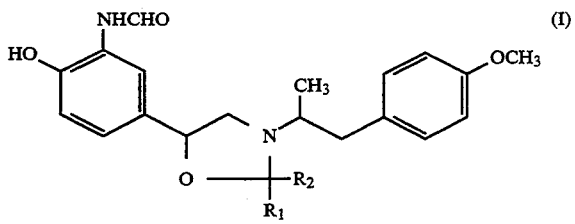

wherein $R_1$ and $R_2$ are simultaneously hydrogen or both are the same lower alkyl radical or together are 4- to 7-membered lower alkylene, and to the salts thereof in racemic and chiral form, to the preparation of these novel compounds, to pharmaceutical compositions containing them and to the use thereof as medicaments.

U.S. Pat. No. 4,407,819 (American Cyanimide Co.) discloses oxazolidines which differ in the orientation of the substituents at the phenyl ring and in the substituents at the oxygen atom in the oxazolidine ring, and which are used as additives for animal feeds.

Throughout this specification, radicals and compounds qualified by the term "lower" will be understood as meaning those that carry up to 7, preferably up to 4, carbon atoms inclusive.

Lower alkyl is typically $C_1$–$C_4$alkyl such as methyl, ethyl, propyl or butyl.

4- to 7-Membered lower alkylene is preferably 1,4-butylene, 1,5-pentylene, 1,6-hexylene, and also 1,7-heptylene.

The novel compounds thus comprise all enantiomers, diastereoisomers and their mixtures, including their racemates. Compounds of formula I within the scope of this invention are preferably in the form of racemates of possible stereoisomers (R,R and S,S), but more preferably in chiral forms R,R and S,S.

Salts of compounds of formula I are preferably pharmaceutically acceptable salts, typically acid addition salts, which are formed, inter alia, with strong inorganic acids such as mineral acids, e.g. sulfuric acid, a phosphoric acid or a hydrohalic acid, with strong organic carboxylic acids such as lower alkanecarboxylic acids, typically acetic acid, or with dicarboxylic acids or unsaturated dicarboxylic acids such as malonic acid, maleic acid or fumaric acid, or with hydroxycarboxylic acids such as tartaric or citric acid, or with sulfonic acids such as lower alkanesulfonic acids or benzenesulfonic acids or substituted benzenesulfonic acids such as methane or p-toluenesulfonic acid, or salts with bases, typically alkali metal or alkaline earth metal salts, e.g. sodium, potassium or magnesium salts, pharmaceutically acceptable transition metal salts such as zinc or copper salts, or salts with ammonia or organic amines, including cyclic amines such as mono-, di- or tri-lower alkylamines, typically hydroxy-lower alkylamines, e.g. mono-, di- or tri-hydroxy-lower alkylamines, hydroxy-lower alkyl-lower alkylamines or polyhydroxy-lower alkylamines. Cyclic amines are typically morpholine, thiomorpholine, piperidine or pyrrolidine. Suitable mono-lower alkylamines typically include ethyl- and tert-butylamine, and suitable di-lower alkylamines are typically diethyl- and diisopropylamine, and suitable tri-lower alkylamines are typically trimethyl- and triethylamine. Corresponding hydroxy-lower alkylamines are typically mono-, di- and triethanolamine; hydroxy-lower alkyl-lower alkylamines are typically N,N-dimethylaminoethanol and N,N-diethylaminoethanol; a suitable polyhydroxy-lower alkylamine is glucosamine. Unsuitable salts are also included for pharmaceutical usages, as these may be used, inter alia, for the isolation and/or purification of free compounds of formula I and their pharmaceutically acceptable salts.

The compounds of formula I and their pharmaceutically acceptable salts have valuable pharmacological properties.

The novel compounds of formula I have a prolonged stimulating action on beta-adrenergic receptors or they induce relaxation of sensitive unstriated muscles.

Owing to this effective relaxation of unstriated muscles, the compounds of formula I can be used for the prevention or treatment of bronchial spasm and dispnoe in diseases such as bronchial asthma, chronic bronchitis and chronic obstructive pulmonary diseases, anaphylactic bronchial spasm and cystic fibrosis as well as for the prevention or alleviation of premature labour pains in a stage of pregnancy.

The compounds of formula I are also useful for the prevention or treatment of inflammatory conditions in a variety of diseases, especially where the activation of beta-adrenergic receptors influences the course of the disease.

In particular, the compounds of formula I are suitable for preventing or limiting the release of preformed or newly synthesised inflammation transmitters of cellular degranulation products and reactive oxygen compounds of cells such as mast cells, macrophages, basophilic cells, eosinophilic cells and lymphocytes.

The compounds of formula I induce an antiinflammatory action by preventing or limiting the release of phlogogens such as histamine, leucotrienes, basic and cationic proteins, tryptanes and chymase, cytokines and the like, and are suitable for the treatment of chronic and acute urticaria, psoriasis, allergic conjunctivitis, acinitis, hay fever, mastocytosis and the like.

By activating endothelial beta-adrenergic receptors the novel compounds are also suitable for preventing or alleviating the consequences and injury caused by increased microvascular permeability and may be used, inter alia, for inflammations caused by inflammation transmitters, surgical operations, injuries, burns and radiation injury. The compounds are therefore suitable for the treatment of diseases that are associated with obstruction of the respiratory tract such as asthma, chronic bronchitis and other pulmonary diseases, intumescences, extravasations resulting from surgical operations, chemical injuries, burns and also radiation injury such as cerebral oedema and other injury resulting from radiotherapy. By activating the signal transduction mechanism which is coupled to beta-adrenergic receptors, for example adenylyl cyclase (but not restricted thereto), the novel compounds prevent the production of cytokines, lymphokines and also monoldnes whose synthesis is regulated by easily influenced signal transduction elements, and they are therefore suitable for the treatment of diseases in which proteins participate as transmitters in the course of the disease, including asthma, septicaemia, inflammations, certain immunological processes and the like.

The compounds of formula I induce a useful relaxation of a smooth muscle of the bronchia, of the uterus, of the vascular system and the like.

This relaxation can be detected as follows: in segments which were taken from the ileum of a guinea pig weighing 300–400 g and incubated in an organ bath in tyrode solution at 38° C. and gassed with a mixture of 95% oxygen and 5% carbon dioxide at a load of 1 g, contractions are induced with synthetic leucotriene D$_4$ (in potassium salt form) or histamine PGE$_{2\alpha}$, thromboxane mimetica or BaCl$_2$ (as depolarising solution) and registered isotonically. The degree of inhibition of the contractions by the test compound is determined after a preliminary incubation of 2 minutes in the form of the IC$_{50}$, which denotes the concentration at which the test contractions are reduced by 50%.

The compounds of formula I have an extremely prolonged action and exhibit excellent activity in vivo. For example, in a bronchoconstriction standard assay using guinea pigs, a pronounced LTD$_4$-antagonistic effect may be observed on administration of an aerosol solution containing c. 0.00001 to c. 1% by weight of test compound. In this test model, male guinea pigs of 400–700 g body weight are anaesthetised intraperitoneally with 1.4 g/kg of urethane and a polyethylene cannula is inserted into the jugular vein. A second polyethylene cannula is inserted into the trachea. Pressure in the oesophagus is recorded by means of a cannula inserted into the oesophagus and connected to a Starham pressure transducer. The animal is placed in an airtight plexiglass chamber which is connected to a No. 000 Fleisch's tube and a Validyne transducer MP 45-1. The flow is measured with this assembly. After the surgical preparation of the test animals, a certain period of time is allowed to elapse so as to allow the pulmonary functions to stabilise. The test compound is then administered in accordance with the following procedure. The test animals are exposed for one minute to a 1% (weight/volume) aerosol solution of the test compound or to distilled water (for control purposes). For all the test compounds that are administered by inhalation, a Monaghan ultrasound spray apparatus (model 670) of which the particle size varies between 1 and 8 microns, the majority being 3 microns, is used. Aqueous solutions are freshly prepared each time and are introduced into the chamber of the spray device using an on-stream drug vial. The spray mist produced is administered to the test animals via a glass chamber of 65 ml capacity which is connected to the trachea by a cannula. At the end of the treatment period, LTD$_4$ (0.3 μg/ml) is administered over a period of 2 minutes using a second Monaghan ultrasound spray apparatus (model 670) and via a similar glass chamber. The reduction in compliance is read off in the third minute after the LTD$_4$ administration and the average value of three animals is compared with the average value of three control animals and the percentage inhibition of compliance (% inhibition) is calculated in accordance with the following formula:

$$\% \text{ inhibition} = 100 - \frac{(100 - \text{compliance preparation}) \cdot 100}{(100 - \text{compliance control})}$$

If different concentrations of active ingredient are tested, the percentage inhibition for each concentration is recorded, the "log concentration" on the abscissa being plotted against the "percentage inhibition" on the ordinate. The IC$_{50}$ is then determined by linear regression analysis.

The compounds of formula I and their pharmaceutically acceptable salts also have the specific and therapeutically very significant advantage of a relatively long duration of efficacy.

Preferred compounds of formula I within the scope of this invention are those wherein R$_1$ and R$_2$ are simultaneously hydrogen or both are the same lower alkyl radical or together are 4- to 5-membered lower alkylene, and their salts in racemic and chiral form.

Particularly preferred compounds of formula I within the scope of this invention are those wherein R$_1$ and R$_2$ are simultaneously hydrogen or both simultaneously are methyl or ethyl, and the pharmaceutically acceptable salts thereof in racemic and chiral form.

Most preferred compounds of formula I within the scope of this invention are those wherein R$_1$ and R$_2$ are simultaneously hydrogen, and the pharmaceutically acceptable salts thereof in racemic and chiral form.

Specifically preferred within the scope of this invention is the racemate obtained in Example 1 of (5R)-5-(3-formylamino-4-hydroxyphenyl)-3-[(2R)-1-(4-methoxyphenyl)prop-2-yl]-oxazolidine and (5S)-5-(3-formylamino-4-hydroxyphenyl)-3-[(2S)-1-(4-methoxyphenyl)prop-2-yl]oxazolidine or the enantiomers in pure form, or a pharmaceutically acceptable salt thereof.

The invention further relates to a process for the preparation of compounds of formula I and the salts thereof, which comprises reacting a compound of formula II

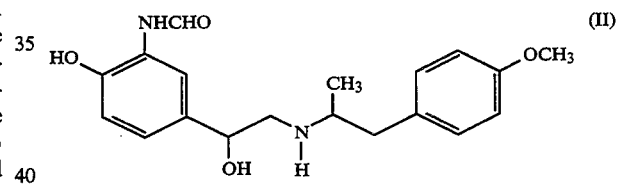

with a compound of formula III

in free and acetalised or ketalised form, wherein R$_1$ and R$_2$ are as defined for formula I.

The condensation of the compounds of formula II with compounds of formula III is carried out in conventional manner in a protic or aprotic solvent such as an aliphatic hydrogen halide, conveniently in a dichloroalkane, preferably methylene chloride, or an aliphatic or cycloaliphafic ether, e.g. in tetrahydrofuran or also dioxane. Other suitable solvents include acetonitrile, ethanol and toluene.

The substances are reacted in the temperature range from −10° to +60° C., preferably from 0° to +30° C., conveniently in the presence of a catalyst, an acid condensing agent, typically an ammonium salt such as ammonium acetate. The starting material of formula II is known and its preparation is described in DE patent 2 305 092 "(corresponding to U.S. Pat. No. 3,994,974)".

The compounds are formula HI are likewise known and described in all textbooks of chemistry as belonging to the stock of common knowledge.

Compounds obtainable by the process of this invention can be converted in conventional manner into compounds of formula I.

Salts of compounds of formula I can be converted in a manner known per se into the free compounds, conveniently by treatment with a base such as an alkali metal hydroxide, a metal carbonate or hydrogencarbonate, or with another salt-forming base referred to at the outset or with an acid, typically a mineral acid, as with hydrochloric acid, or with another salt-fondling acid referred to at the outset.

Salts of compounds of formula I can be converted in a manner known per se into other salts, conveniently by treatment with a suitable metal salt, typically a sodium, barium or silver salt, of another acid in a suitable solvent in which a resultant inorganic salt is insoluble and is thus eliminated from the equilibrium of reaction, and salts of bases by generating the free acid and repeated salt-formation.

The compounds of formula I, including their salts, may also be obtained in the form of hydrates or include the solvent used for crystallisation.

Because of the close relationship between the novel compounds in the free form and in the form of their salts, the references made throughout this specification to the free compounds and their salts will also apply by analogy to the corresponding salts and free compounds.

Depending on the choice of starting materials and procedures, the compounds of formula I and their salts may be obtained in the form of one of the mixtures of diastereoisomers, racemates and enantiomers or as mixtures thereof.

Racemates are separated into the individual enantiomers by column chromatography via a chiral stationary phase.

Racemates can also be separated by known methods into the optical antipodes, conveniently by recrystallisation from an optically active solvent, with the aid of micro-organisms or by reacting the mixture of diastereoisomers or racemate with an optically active compound, e.g. depending on the acid, basic or functionally modifiable groups present in the compound of formula I, with an optically active acid, base or an optically active alcohol, into mixtures of diastereoisomeric salts or functional derivatives such as esters, separating these into the diastereoisomers from which the respective desired enantiomer can be set free in the respective usual manner. Bases, acids or alcohols suitable for the purpose are typically optically active alkaloid bases such as strychine, cinchonine or brucine, or D- or L-(1-phenyl)ethylamine, 3-pipecoline, ephedrine, amphetamine or similar bases which are obtainably by synthesis, optically active carboxylic or sulfonic acids such as quinic acid or D- or L-tartaric acid, D- or L-di-o-toluyl-tartaric acid, D- or L-malic acid, D- or L-mandelic acid or D- or L-camphorsulfonic acid, or optically active alcohols such as borneol or D- or L-(1-phenyl)ethanol.

The invention relates also to those embodiments of the process in which a compound obtainable as intermediate in any stage of the process is used as starting material and the remaining steps are carried out, or a starting material is used in the form of a derivative or a salt or, especially, is formed under the reaction conditions.

The invention also relates to the novel starting materials which have been specially developed for the preparation of the novel compounds, especially those which result in the compounds I described at the beginning as being especially preferred, to processes for their preparation and to the use thereof as intermediates.

The pharmaceutical compositions of this invention which contain the compound of formula I or a pharmaceutically acceptable salt thereof are those for enteral, e.g. oral, and also rectal and parenteral administration to warm-blooded animals, and they contain the pharmacologically active compound alone or together with a pharmaceutically acceptable carrier. The daily dose will depend on the age, sex and individual condition of the patient as well as on the mode of administration.

The compounds of formula I can be formulated for administration in any suitable manner. The invention relates to medicaments which contain at least one compound of formula I or a physiologically acceptable salt thereof and which are formulated for use in human or veterinary medicine. Such compositions may be formulated together with physiologically acceptable carriers or excipients and with additional optional medicaments.

The compounds of formula I can be formulated for administration by inhalation or insufflation, or for oral, buccal, parenteral, topical (including nasal) or rectal administration. Administration by inhalation or insufflation is preferred.

For administration by inhalation, the compounds of formula I are conveniently used in the form of a pressurised aerosol spray pack using a suitable propellant gas.

Such propellant gases or gas mixtures are known per se for the preparation of pharmaceutical aerosols, and typically include saturated hydrocarbons such as n-propane, n-butane or isobutane or n-fixtures thereof or partially fluorinated or completely fluorinated (perfluorinated) hydrocarbons.

Partially fluorinated hydrocarbons are derived from aliphatic hydrocarbons containing preferably 1 to 4 carbon atoms, typically methane, ethane, propane, n-butane or isobutane, or cycloaliphatic hydrocarbons containing preferably 3 and 4 carbon atoms, typically cyclopropane or cyclobutane, the hydrogen atoms being substituted by at least one fluorine atom and, preferably, at least two fluorine atoms, such that at least one hydrogen atom and thus one hydrocarbon bond remains in the molecule.

Completely fluorinated (perfluorinated) hydrocarbons are derived from the above mentioned aliphatic hydrocarbons of 1 to 4 carbon atoms and the cycloaliphatic hydrocarbons of 3 to 4 carbon atoms by substitution of the hydrogen atoms by fluorine atoms.

Suitable partially or completely fluorinated hydrocarbons are typically methane derivatives containing 1 to 4, ethane derivatives containing 1 to 6, propane derivatives containing 1 to 8, n-butane derivatives containing 1 to 10, cyclopropane derivatives containing 1 to 6 and cyclobutane derivatives containing 1 to 8, fluorine atoms. In these partially or completely fluorinated hydrocarbons the hydrogen atoms are in different positions of the hydrocarbon molecule. The following possibilities of isomerism exist for partially fluorinated hydrocarbons:

If there is only one hydrogen atom in the hydrocarbon molecule, in propane and butane derivatives it may be in terminal position or at a connecting member of the carbon chain.

Where the hydrocarbon molecule contains more than one hydrogen atom, still further possibilities of isomerism exist for ethane, propane, n-butane, cyclopropane and cyclobutane derivatives as well as for hydrocarbons containing a greater number of carbon atoms. The hydrogen atoms may be partially or completely in terminal position and be partially or completely at one member or at different connecting members of the carbon chains. "Mixed" possibilities of isomerism are also possible, where the hydrogen atoms of aliphatic derivatives are differently distributed on the terminal carbon atoms and on the same or different connecting members of the carbon chain or are on the same or different carbon ring members of cycloaliphatic derivatives.

It is common practice to use code designations to abbreviate the customary nomenclature and to distinguish between the partially fluorinated hydrocarbons as well as the completely fluorinated hydrocarbons referred to hereinafter. These code designations are explained in Pharmazeutische Technologie, H. Sucker, P. Fuch, P. Speiser (Editor), Thieme Verlag, D-7000 Stuttgart 1978, on page 735, and are likewise applicable to CFCs. It is customary to use suffixes with the letters a, b . . . for the numerous possibilities of isomerism referred to.

Preferred partially fluorinated hydrocarbons are tetrafluoroethane (134 and 134a), trifluoroethane (143a), difluoroethane (152 and 152a) and heptafluoropropane (227).

Alternatively, the compounds of formula I for administration by inhalation or insufflation may be in the form of a dry powder, conveniently as powder mixture, of the compound and a suitable powder base material such as lactose or starch. The powder mixture can be in unit dose form, typically in the form of capsules or cartridges of e.g. gelatin, or in the form of blister packs from which the powder can be released by mans of an inhaler or an insufflater.

For oral administration, the pharmaceutical compositions may typically be in the form of tablets, capsules, powders, solutions, syrups or suspensions which are prepared by known methods with acceptable diluents or medicinal carriers. For buccal administration, the composition may be in the form of tablets, drops or lozenges, which are prepared in known manner.

The compounds of formula I can also be administered parenterally. Compositions for injection may be in unit dose form in ampoules or in multiple dosage containers with added preservatives. The fomulations may be in the form of suspensions, solutions or emulsions in oil or aqueous vehicles and can contain adjuvants such as suspending agents, stabilisers and/or dispersants. Alternatively, prior to use the active compound may be in powder form for reconstitution with a suitable carrier, typically sterilised, pyrogen-free water.

For topical application, the pharmaceutical compositions of this invention may be in the form of ointments, lotions or creams which are prepared in per se known manner, conveniently with an aqueous or oily base, normally by adding suitable thickeners and/or solvents. For nasal application, the compositions can be in the form of a spray which may be prepared as an aqueous solution or suspension or as an aerosol with a suitable propellant.

The compounds of formula I can also be in the form of compositions for rectal administration such as suppositories or retention enemas, conveniently those that contain suppository bases such as cocoa butter or other glycerides.

If the pharmaceutical compositions are prescribed for oral, buccal, rectal or topical administration, they may be associated in per se known manner with dosage forms that permit a controlled or delayed release.

The contemplated daily dose of active compound for oral administration in the treatment of humans is 10 to 500 $\mu$g, which may suitably be administered as a single dose. The exact dose will naturally depend on the age and condition of the patient and on the mode of administration. Suitable doses for administration by inhalation (aerosols) or nasal application are from 1–200 $\mu$g, for rectal administration from 10 to 500 $\mu$g, for intravenous administration from 0.01 to 100 $\mu$g, and for topical application from 1 to 1000 $\mu$g.

The following Examples will serve to illustrate the invention. Pressures are given in millibars.

EXAMPLE 1

With stirring, 1.0 ml of 36.5% aqueous formaldehyde is added at room temperature to a suspension of 2.75 g of 2'-hydroxy-5'-[(RS)-1-hydroxy-2-[[(RS)-p-methoxy-$\alpha$-methylphenylethyl]amino]ethyl]formanilide (racemic mixture of R,R- and S,S-enantiomers) in 80 ml of methylene chloride. The mixture is stirred for 30 minutes, whereupon a solution forms. The solution is stirred for a further 15 hours at 26° C. The precipitated crystals are isolated by filtration, washed with a small amount of methylene chloride and dried at 40° C./0.1 mbar for 15 hours. After recrystallisation from ethyl acetate, the racemate of (5R)-5-(3-formylamino-4-hydroxyphenyl)-3-[(2R)-1-(4-methoxyphenyl)prop-2-yl]oxazolidine and (5S)-5-(3-formylamino-4-hydroxyphenyl)-3-[(2S)-1-(4-methoxyphenyl)prop-2-yl]oxazolidine melts at 87°–92° C., [$^1$H-NMR (400 MHZ, CDCl$_3$: 8.27 (d, 1H), 7.75 (b, 1H), 7.31 (d, 1H), 7.10 (m, 2H), 7.08 (d, d, 1H), 6.93 (d, 1H), 6.85 (m, 2H), 5.00 (t, 1H), 4.63 (AB system, 2 H), 3.81 (S, 3H), 3.43 and 2.80 (d, d/d, d, 2H), 2.81 (m, 1H), 2.93 and 2.51 (d, d/d, d, 2H). 1,04 (d, 3H)].

EXAMPLE 2

With stirring, a mixture of 2.0 g of 2'-hydroxy-5'-[(R,S)-1-hydroxy-2-[[(R,S)-p-methoxy-$\alpha$-methylphenylethyl]amino]ethyl]formanilide (racemic mixture of R,R- and S,S-enantiomers), 200 ml of 2,2-dimethoxypropane and 6.0 g ammonium acetate in 140 ml of acetone is refluxed for 15 hours, then cooled and concentrated under 11 mbar to dryness. To the residue are added 10.0 g of potassium hydrogencarbonate, 50 ml of ice/water and 50 ml of methylene chloride. After shaking vigorously, the organic phase is separated, washed with 10 ml of 2N potassium hydrogencarbonate and with 10 ml of brine, dried over magnesium sulfate, and concentrated by evaporation at 40° C./11 mbar. The residue is flash chromatographed on 70 g of silica gel. The fractions 1–8, each eluted with 100 ml of methylene chloride/methanol (98:2), are discarded. The fractions 9–14, each eluted with 100 ml of methylene chloride/methanol (98:2), are combined and concentrated by evaporation at 40° C./11 mbar. The residue, the racemic mixture of 2,2-di-methyl-(5R)-5-(3-formylamino-4-hydroxyphenyl)-3-[(2R)- 1-(4-methoxyphenyl)prop-2-yl]oxazolidine and 2,2-dimethyl-(5S)-5-(3-formylamino-4-hydroxyphenyl)-3-[(2S)-1-(4 -methoxyphenyl)prop-2-yl]oxazolidine, is obtained as an amorphous powder. [$^1$NMR(400 MHZ, CD Cl$_3$; 8.42 (b, 1H), 8.29 (b, 1H), 7.66 (d, b, 1H), 7.10 (m, 2H), 6.87 (m, 2H), 6.81 (d, d, 1H), 6.57 (d, 1H), 4.84 (t, 1H), 3.82 (s, 3H), 3.10 . . . 2.66 (m, 5H), 1.28 and 1.11 (2s, 2×3H), 1.18 (d, 3H)].

EXAMPLE 3

The RR- and SS-enantiomers of the racemic mixture obtained according to Example 1 are obtained as follows: 20 μl of a 0.1% solution of the racemic mixture of Example 1 are injected into a chiral "CHIRALCEL OJ" (Daicel Chemical Industries, Japan) HPLC column. The carrier material consists of silica gel loaded with para-methylbenzoyl cellulose. At a ram of flow of 1 ml/min and with an eluant consisting of hexane (85 vol %) and 2-propanol (15 vol %), the enantiomers are separated with a separation factor of α=1.27.

EXAMPLE 4

20 μl of a 1% solution of the racemic mixture obtained according to Example 1 are injected into a chiral meta-methylbenzoyl cellulose (preparation in accordance with EP-A-0 316 270"U.S. Pat. No. 5,066,793 and U.S. Pat. No. 5,091,520"). HPLC column. At a rate of flow of 1 ml/min and with an eluant consisting of hexane (85 vol %) and 2-propanol (15 vol %), the enantiomers are separated with a separation factor of α=1.18.

EXAMPLE 5

With stirring, 22 μl of 37% aqueous formaldehyde are added at room temperature to a solution of 99.5 mg of (−)-2'-hydroxy-5'-(R)- 1 -hydroxy-2-[[(R)-p-methoxy-α-methylphenethyl]amino]ethyl]formanilide (R,R-enantiomer) in 3 ml of methylene chloride. The mixture is stirred for 15 hours at 5°–15° C., wherupon a solution forms. The solution is diluted with 3 ml of methylene chloride, the methylene chloride phase is washed with water (2×2 ml), dried over magnesium sulfate and concentrated by evaporation at 40° C./20 mbar. The residue is dried at 25° C./0.1 mbar for 15 hours, giving (−)-(5R)-5-(3-formylamino-4-hydroxyphenyl)-3-[(2R)-1-(4-methoxyphenyl)prop-2-yl]-oxazolidine as a white amorphous solid. [$^1$H-NMR (400 MHZ, CD$_2$Cl$_2$: 8.24 (d, 1H), 7.70 (b,1H), 7.21 (d, 1H), 7.10 (m,2H), 7.09 (d,d,1 H), 6.93 (d. 1H), 6.83 (m,2H), 4.94 (+,1H), 4,57 (AB,2H), 3.78 (s,3H), 3.40 und 2.75 (2d,d,2H), 2.88 und 2,50 (2d,d,2H), 2.79 (m, 1H),1.00 (d,3H)].

[α]$^{20}_D$= −13.1±1.9° (c=0.518, MeOH)

EXAMPLE 6

With stirring, 33.28 μl of 37% aqueous formaldehyde are added at 5°–15° C. to a solution of 151 mg of (−)-2'-hydroxy-5'-(S)-1-hydroxy-2-[[(S)-p-methoxy-α-methylphenethyl]amino]ethyl]formanilide (S,S enantiomer) in 4.5 ml of methylene chloride. The mixture is stirred for 15 hours at 5°–15° C., whereupon a solution forms. The solution is diluted with 4 ml of methylene chloride, the methylene chloride phase is washed with water (2×3 ml), dried over magnesium sulfate and concentrated by evaporation at 40° C./15 mbar. The residue is dried at 25° C./0.1 mbar for 15 hours, giving (−)-(5S)-5-(-3-formylamino-4-hydroxyphenyl)-3-[(2S)-1-(4-methoxyphenyl)prop-2-yl]oxazolidine as an amorphous powder. [$^1$H-NMR (400 MHZ, CD$_2$Cl$_2$)]: identical with the spectrum of the compound of Example 5.

[α]$^{20}_D$= +17.3±1.8° (c=0.550, MeOH)

Analytical determination of the optical purity of the enantiomers

The analytic determination of the purity of the enantiomers (R,R) (Example 5) and (S,S) (Example 6) was made by HPLC on the chiral column (0.46 cm×25 cm) Chiracel OJ (Daicel Chemical Industries, Japan) with a mixture of hexane (85 vol %) and ethanol (15 vol %) as eluant, and at a rate of flow of 1 mil/min. The chromatography apparatus consists of a pump (Gilson, Modell 303), an autosampler (Shimadzu SLC-6B9), a variable UV detector (Perkin-Elmer LC-95) and a data recording system (Metrohm AG, IC-Metrodata 7 14). 20 microlitres of a 0.1% solution (in ethanol) of the individual enantiomers were injected into the column and the following results were obtained (detection at 240 nm): (+) (S,S) enantiomer (compound of Example 6), retention time 93.31 min, ee>99.9%; (−) (R,R) enantiomer (compound of Example 5), retention time 115.89 min, ee>99.9%.

What is claimed is:

1. A compound of formula (I)

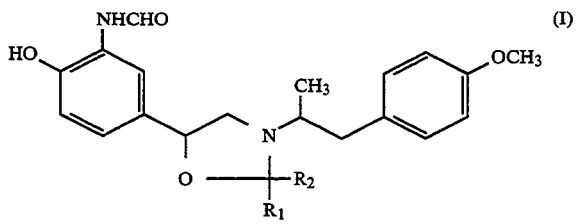

wherein R$_1$ and R$_2$ are simultaneously hydrogen or both are the same lower alkyl radical or together are 4- to 7-membered lower alkylene, or a pharmaceutically acceptable salt thereof in racemic or chiral form.

2. A compound of formula I according to claim 1, wherein R$_1$ and R$_2$ are simultaneously hydrogen or both are the same lower alkyl radical or together are 4- to 5-membered lower alkylene, or a pharmaceutically acceptable salt thereof in racemic or chiral form.

3. A compound of formula I according to claim 1, wherein R$_1$ and R$_2$ are simultaneously hydrogen or both simultaneously are methyl or ethyl, or a pharmaceutically acceptable salt thereof in racemic or chiral form.

4. A compound of formula I according to claim 1, wherein R$_1$ and R$_2$ are simultaneously hydrogen, or a pharmaceutically acceptable salt thereof in racemic or chiral form.

5. The compound of claim 1 which is selected from the group consisting of (a) (5R)-5-(3-Formylamino-4-hydroxyphenyl)-3-[(2R)-1-(4-methoxyphenyl)prop-2-yl]oxazolidine, (b) (5S)-5-(3-Formylamino-4-hydroxyphenyl)-3-[(2S)-1-(4-methoxyphenyl)prop-2-yl]oxazolidine, and (c)the racemate of (5R)-5-(3-formylamino-4-hydroxyphenyl)-3-[(2R)-1-(4-methoxyphenyl)prop-2-yl]oxazolidine, and (5S )-5-(3-formylamino-4-hydroxyphenyl)-3-[(2S)-1-(4-methoxyphenyl)prop-2-yl]oxazolidine, or a pharmaceutically acceptable salt thereof.

6. A method of stimulating beta-adrenergic receptors in an animal in need thereof comprising administering to said animal a beta-adrenergic receptor stimulating amount of a compound of claim 1 or a pharmaceutically acceptable salt thereof in racemic or in chiral form.

7. A pharmaceutical composition for the stimulation of beta-adrenergic receptors in an animal comprising a beta-adrenergic receptor stimulating effective mount of a compound according to claim 1 or a pharmaceutically acceptable salt thereof, in racemic or in chiral form, and a pharmaceutically acceptable carrier therefor.

* * * * *